United States Patent [19]

Merz et al.

[11] Patent Number: 6,034,278
[45] Date of Patent: Mar. 7, 2000

[54] METHOD FOR PRODUCING OPTICALLY ACTIVE 1-PHENYLETHYLAMINES

[75] Inventors: Walter Merz; Martin Littmann; Udo Kraatz; Christoph Mannheims, all of Leverkusen, Germany

[73] Assignee: Bayer Aktiengesellschaft, Leverkusen, Germany

[21] Appl. No.: 09/194,719

[22] PCT Filed: Jun. 9, 1997

[86] PCT No.: PCT/EP97/02988

§ 371 Date: Dec. 17, 1998

§ 102(e) Date: Dec. 17, 1998

[87] PCT Pub. No.: WO97/49665

PCT Pub. Date: Dec. 31, 1997

[30] Foreign Application Priority Data

Jun. 21, 1996 [DE] Germany .................. 196 24 820

[51] Int. Cl.[7] .................................................. C07C 209/00
[52] U.S. Cl. ...................... 564/438; 564/302; 564/304
[58] Field of Search .................... 564/438, 302, 564/304

[56] References Cited

U.S. PATENT DOCUMENTS 4,874,420  10/1989  Wroblowsky et al. .
4,988,734   1/1991  Kraatz et al. .
5,144,077   9/1992  Jansen et al. .
5,183,939   2/1993  Jansen et al. .

FOREIGN PATENT DOCUMENTS 257448  3/1998  European Pat. Off. .

OTHER PUBLICATIONS

E. Brown et al, Tetrahedron Letters, vol. 26, No. 37, (month unavailable) 1985, pp. 4451–4452.

*Primary Examiner*—Paul J. Killos
*Attorney, Agent, or Firm*—Joseph C. Gil; Carol Marmo

[57] ABSTRACT

The invention concerns a new method for producing optically active 1-phenylethylamines, wherein (a) racemic 1-phenylethylamines are reacted with (S)-(–)-N-phenylcarbamate lactic acid in the presence of an aliphatic or aromatic hydrocarbon and in the presence of a lower aliphatic alcohol, wherein the reaction components are measured so that for every mole of racemic amine, between 0.25 and 0.5 mole of (S)-(–)-N-phenylcarbamate lactic acid are present, the reaction mixture is then concentrated at a liquid-phase temperature of up to 40° C., the resulting solid product is separated, treated with diluted, aqueous alkaline lye in the presence of a hydrocarbon, and the respective (R)-amine is isolated by distillation from the organic phase, and if necessary, (b) the mother liquor remaining after the separation of the solid product is reacted in the presence of a lower aliphatic alcohol with (S)-(–)-N-phenylcarbamate lactic acid, wherein the reaction components are measured so that the molar quantity of (S)-(–)-N-phenylcarbamate lactic acid is twice as great as the quantity of (R)-amine still remaining in the mother liquor, the reaction mixture is then concentrated at a liquid-phase temperature of up to 40° C., the resulting solid product is separated and the (S)-amine is isolated by distillation from the mother liquor.

10 Claims, No Drawings

METHOD FOR PRODUCING OPTICALLY ACTIVE 1-PHENYLETHYLAMINES

TECHNICAL FIELD OF THE INVENTION

The present invention relates to a novel process for the preparation of known, optically active 1-phenylethylamines, which can be used as intermediates for the synthesis of active ingredients having fungicidal or pharmacological properties.

BACKGROUND OF THE INVENTION

It is already known that (R)-1-(4-chloro-phenyl)-ethylamine can be prepared by reacting racemic 1-(4-chloro-phenyl)-ethylamine with (S)-(−)-N-phenylcarbamate lactic acid in the presence of ethanol, filtering off the resulting crystal sludge with suction and treating it with aqueous sodium hydroxide solution in the presence of methylene chloride (cf. EP-A 0 341 475). A disadvantage of this process is that there is a considerable amount of S-(−)-phenylcarbamate lactic acid in the mother liquor which results after the crystal sludge has been filtered off with suction, which can only be isolated from the liquor in a complex method.

Furthermore, it is already known that (S)-1-(4-chloro-phenyl)-ethylamine can be obtained by reducing the mother liquor which forms during the abovementioned process by distilling off ethanol, stirring the remaining residue with tert-butyl methyl ether or toluene, separating off the crystalline salt which separates out and distilling the mother liquor (cf, DE-A 4 039 447). However, this process is too expensive to be carried out on an industrial scale.

DETAILED DESCRIPTION OF THE INVENTION

It has now been found that optically active 1-phenyl-ethyl-amines of the formula

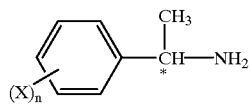
(I*)

in which

X is halogen or methyl, and n is 0, 1 or 2, can be obtained in separate form from racemic 1-phenyl-ethyl-amines using (S)-(−)-N-phenylcarbamate lactic acid, if a) racemic 1-phenyl-ethylamines of the formula

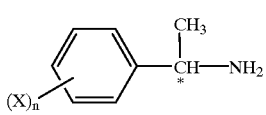
(I)

in which

X and n are as defined above are reacted with (S)-(−)-N-phenylcarbamate lactic acid of the formula

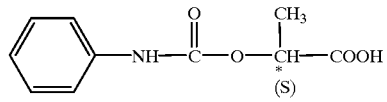
(II)

in the presence of an aliphatic or aromatic hydrocarbon and in the presence of a lower aliphatic alcohol, the amounts of the reaction components being such that per 1 mol of racemic 1-phenyl-ethyl-amine of the formula (I), between 0.25 and 0.5 mol of (S)-(−)-N-phenylcarbamate lactic acid of the formula (II) are present, then the lower aliphatic alcohol and, where appropriate, some of the aliphatic or aromatic hydrocarbon are distilled off at a sump temperature up to 40° C., option ally under reduced pressure, the resulting crystalline product of the formula

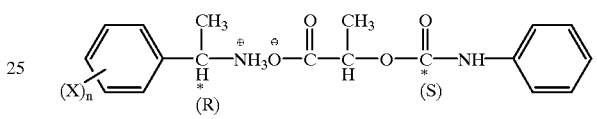
(III-a)

in which

X and n are as defined above, is separated off, stirred with dilute, aqueous alkaline solution in the presence of an aliphatic or aromatic hydrocarbon, the organic phase is separated off, the aqueous phase is again stirred with an aliphatic or aromatic hydrocarbon, the organic phase is again separated off and the combined organic phases are distilled to isolate the (R)-1-phenyl-ethylamine of the formula

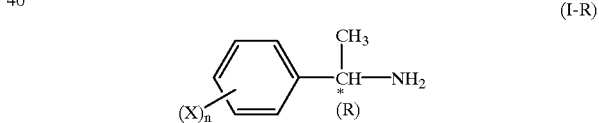
(I-R)

in which

X and n are as defined above which is produced in each case and optionally b) the mother liquor which remains after the salt of the formula (III-a) has been separated off is reacted, in the presence of a lower aliphatic alcohol, with (S)-(−)-N-phenylcarbamate lactic acid of the formula

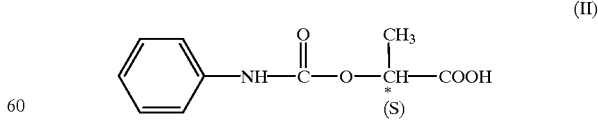
(II)

where the amounts of the reaction components are such that the molar amount of (S)-(−)-N-phenylcarbamate lactic acid of the formula (II) is twice the amount of (R)-1-phenyl-ethylamine of the formula (I-R) still present in the mother liquor, then the lower aliphatic alcohol and, where appropriate, some of the aliphatic or aromatic hydrocarbon, are distilled at a sum, temperature up to 40° C., optionally under reduced pressure, the resulting crystalline product of the formula

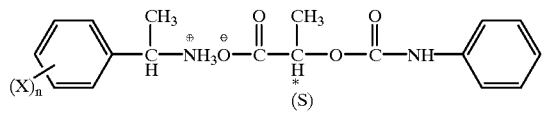

(III-b)

in which
X and n are as defined above
is separated off, and the mother liquor which remains is distilled to isolate the (S)-1-phenyl-ethylamine of the formula

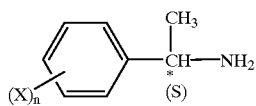

(I-S)

in which
X and n are as defined above,
which is produced in each case.

To denote optically active compounds, the chiral centres in the above formulae and in what follows are marked in each case by (*). The configuration of the asymmetrically substituted carbon atoms is given by the symbols (R) or (S).

It should be pointed out that it is particularly surprising that (R)-1-phenyl-ethylamines of the formula (I-R) can be prepared by the process according to the invention in extremely high yield and excellent optical purity. On the basis of the known prior art, it could not have been expected that the respective salt of (R)-1-phenyl-ethylamine and (S)-(-)-N-phenylcarbamate lactic acid would form preferentially from the hydrocarbon present following distillation of the lower aliphatic alcohol, since the salts of (R)-1-phenyl-ethylamines and (S)-(-)-N-phenylcarbamate lactic acid and also the salts of (S)-1-phenyl-ethylamines and (S)-(-)-N-phenylcarbamate lactic acid are equally sparingly soluble in the hydrocarbon. It is also unexpected that it is possible to precipitate the corresponding salt of the racemic 1-phenyl-ethylamine in virtually quantitative amounts from the mother liquor obtained after the salt of the formula (III-a) has been separated off by adding more (S)-(-)-phenylcarbamate lactic acid, and that it is possible to isolate the corresponding (S)-1-phenyl-ethylamine in high optical purity from the filtrate. What is most surprising is that the crystallization behaviour of the isomeric salts is entirely different when the process is carried out according to the invention in two stages from that which is observed during the analogous single-stage reaction. If racemic 1-(4-chloro-phenyl)-ethylamine is reacted with any desired amounts of (S)-(-)-N-phenylcarbamate lactic acid in a single stage, then after the salt has been separated off, it is never possible to isolate the (S)-1-(4-chloro-phenyl)-ethylamine present in the mother liquor in high optical purity. Moreover, it could not be predicted that the process according to the invention only proceeds in the desired manner if the reaction components are used in the molar amounts specifically given.

The process according to the invention is characterized by a number of advantages. It permits, as already mentioned, the preparation of (R)-1-phenyl-ethylamines of the formula (I-R) in extremely high yield and excellent purity. It is particularly advantageous that the (S)-(-)-N-phenylcarbamate lactic acid used can be recovered in a simple manner in virtually quantitative amounts and be used again. Moreover, racemate resolution according to the invention is considerably less complex than the corresponding methods known previously. It is also favourable that the mother liquor which forms after the salt has been separated off in the second reaction stage contains virtually all of the respective (S)-1-phenyl-ethylamine, and trouble-free isolation of these substances is possible. Finally, it is possible, without problem, to recover most of the racemic 1-phenyl-ethylamine present in the salt separated off in the second stage.

If 1 mol of racemic 1-(4-chlorophenyl)-ethylamine is reacted in the first stage with 0.45 mol of (S)-(-)-N-phenylcarbamate lactic acid in the presence of toluene and methanol, aqueous sodium hydroxide solution is used to liberate the (R)-1-(4-chlorophenyl)-ethylamine and, in the second stage, reaction is carried out with 0.2 mol of (S)-(-)-N-phenylcarbamate lactic acid in the presence of toluene and methanol, then the progress of the process according to the invention can be illustrated by the following equation:

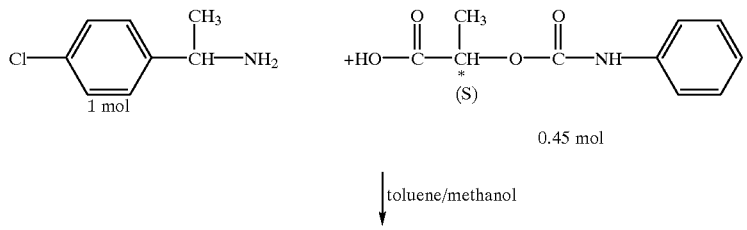

-continued crystals

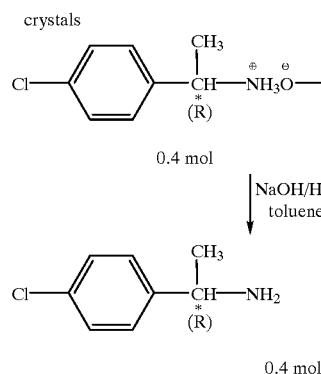

0.4 mol

↓ NaOH/H₂O
toluene

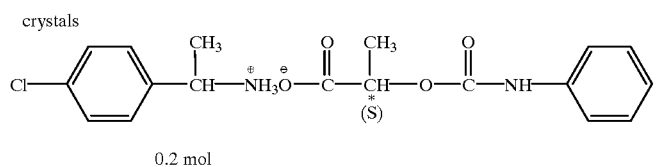

0.2 mol mother liquor

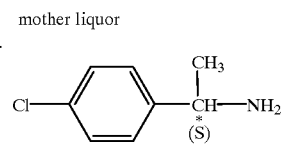

0.4 mol

0.2 mol racemic

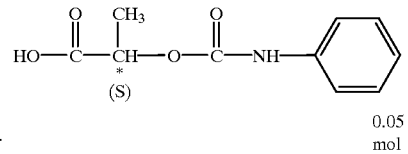

0.05 mol

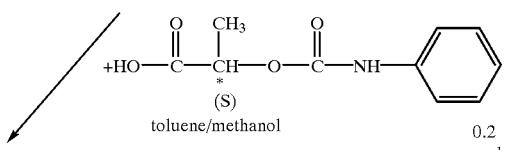

0.2 mol mother liquor

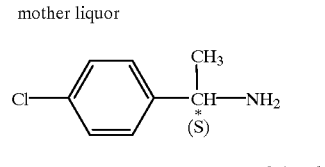

0.4 mol

The racemic 1-phenyl-ethylamines required as starting substances for carrying out the process according to the invention are defined by the formula (I). In this formula, X is preferably fluorine, chlorine, bromine or methyl. The index n is 0, 1 or 2.

The following compounds may be mentioned as examples of racemic 1-phenyl-ethylamines of the formula (I):

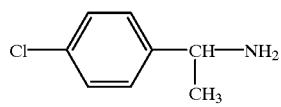

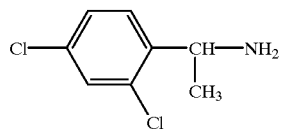

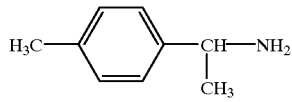

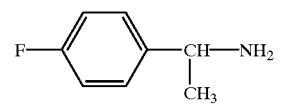

-continued

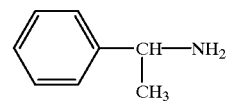

Racemic 1-phenyl-ethylamines of the formula (I) are known (cf. EP-A 0 341 475).

The (S)-(−)-N-phenylcarbamate lactic acid of the formula (II) required as a reaction component for carrying out the process according to the invention is likewise known (cf. EP-A 0 341 475).

Suitable hydrocarbons both for carrying out the first and also the second stage of the process according to the invention are preferably toluene or methylcyclohexane. A suitable lower aliphatic alcohol both for the reaction in the first and also in the second stage is preferably methanol.

Suitable alkaline solutions for liberating the (R)-1-phenyl-ethylamines from the salts produced in the first stage are preferably aqueous sodium hydroxide solution or aqueous potassium hydroxide solution.

The reaction temperatures can be varied within a certain range when carrying out the process according to the invention. Both the first and also the second stage are generally carried out at temperatures between −20° C. and +40° C., preferably between 10° C. and 40° C. During removal of the lower aliphatic alcohol, the reaction mixture is generally heated to a temperature of 40° C., preferably to 30° C. The respective (R)-1-phenyl-ethylamine is generally liberated from the corresponding salt at temperatures between 0° C. and 50° C., preferably between 0° C. and 30° C.

Both the first and also the second stage of the process according to the invention are generally carried out under atmospheric pressure. However, the lower aliphatic alcohol is preferably removed under reduced pressure.

When carrying out the process according to the invention, the ratio of reaction components can be varied in a certain range. Per 1 mol of a racemic 1-phenyl-ethylamine of the formula (I), the first stage is generally carried out using between 0.25 and 0.50 mol, preferably between 0.40 and 0.475 mol, of (S)-(−)-N-phenylcarbamate lactic acid of the formula (II). When carrying out the first stage of the process according to the invention, the amount of hydrocarbon can likewise be varied within a certain range. Per 1 mol of racemic 1-phenyl-ethylamine of the formula (I), between 0.5 and 2 kg, preferably between 0.75 and 1.5 kg, of hydrocarbon are generally used.

In carrying out the process according to the invention, the reaction components can be added together in any order. The (S)-(−)-N-phenylcarbamate lactic acid of the formula (II) can be added in solid form or else dissolved in a lower aliphatic alcohol, optionally mixed with an aliphatic or aromatic hydrocarbon.

For the sake of completeness, it should be pointed out that the (S)-(−)-N-phenylcarbamate lactic acid of the formula (II) which is present in the mother liquor following liberation of the respective (R)-1-phenyl-ethylamine, can be precipitated out by adding dilute mineral acid, such as, for example, dilute sulphuric acid or dilute hydrochloric acid, and, after filtering and drying, can be reused. In a corresponding manner, the (S)-(−)-N-phenylcarbamate lactic acid can be isolated from the salt of the racemic 1-phenyl-ethylamine produced in the second stage.

The (R)-1-phenyl-ethylamines of the formula (I-R) which can be prepared by the process according to the invention are useful intermediates for the synthesis of active ingredients having fungicidal properties (cf. EP-A 0 341 475). For example, the diastereomer mixture of N-(R)-[1-(4-chloro-phenyl)-ethyl]-(1R)-2,2-dichloro-1-ethyl-3t-methyl-1r-cyclopropanecarboxamide and N-(R)-[1-(4-chloro-phenyl)-ethyl]-(1S)-2,2-dichloro-1-ethyl-3t-methyl-1r-cyclopropanecarboxamide of the formulae

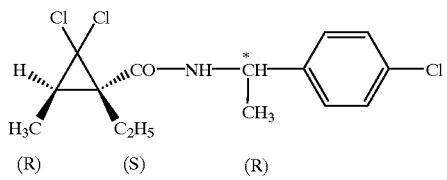

(IV-a)

and

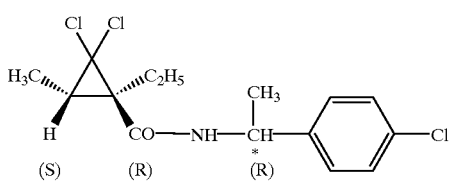

(IV-b)

can be prepared by reacting a 1:1 mixture of (1R)-2,2-dichloro-1-ethyl-3t-methyl-1r-cyclopropanecarbonyl chloride and (1S)-2,2-dichloro-1-ethyl-3t-methyl-1r-cyclopropanecarbonyl chloride of the formulae

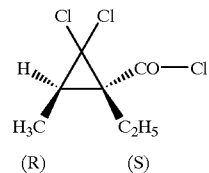

(Va)

and

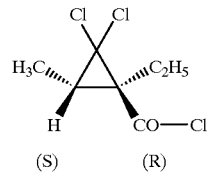

(Vb)

with (R)-1-(4-chloro-phenyl)-ethylamine of the formula

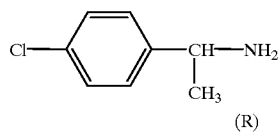

(I-R-1)

in the presence of a diluent, such as methylene chloride, and in the presence of an acid-binding agent, such as triethylamine.

The (S)-1-phenyl-ethylamines of the formula (I-S), which can also be prepared by the process according to the invention, are likewise useful intermediates. They can be used for the synthesis of substances having fungicidal or pharmacological properties (cf. EP-A 0 257 448 and EP-A 0 300 313). It is also possible to racemize the (S)-1-phenyl-ethylamines of the formula (I-S) and reuse them for racemate resolution (cf. EP-A 0 489 682).

Implementation of the process according to the invention is illustrated by the following examples.

PREPARATION EXAMPLES

Example 1

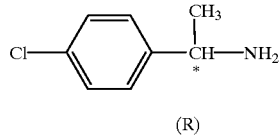

(I-R-1)

18.8 kg (90 mol) of (S)-(−)-N-phenylcarbamate lactic acid are added to a mixture of 120 kg of methanol and 80 kg of toluene at room temperature. The mixture is heated to 30° C. with stirring, and 31.1 kg (200 mol) of racemic 1-(4-chlorophenyl)-ethylamine are added thereto. A mixture of methanol and toluene is then distilled off at a constant sump temperature of 30° C. with gradual reduction of the pressure to from 90 to 100 mbar until the gas-chromatographic check shows that the bottom product is free from methanol. During distillation, 200 kg of toluene are simultaneously added in order to still be able to stir the suspension which forms and to keep the volume of the reaction mixture virtually constant. The reaction mixture is then cooled to 0° C. and filtered with suction. The solid which forms is washed 2×45 kg of toluene and then dried. This gives 32.8 kg of product, 95% of which is the salt of (R)-1-(4-chloro-phenyl)-ethylamine with (S)-(−)-N-phenylcarbamate lactic acid.

Liberation of (R)-1-(4-chloro-phenyl)-ethylamine

The abovementioned salt is stirred with 95 kg of 4% strength of aqueous sodium hydroxide solution in the presence of toluene at room temperature. After the salt has completely dissolved, the organic phase is separated off. The aqueous phase is extracted twice with toluene. The combined organic phases are distilled under reduced pressure. This gives 13.7 kg of (R)-1-(4-chloro-phenyl)-ethylamine (R:S ratio=96:4).

Recovery of (S)-(−)-N-phenylcarbamate Lactic Acid 12 kg of aqueous hydrochloric acid (30% strength) are added at room temperature to the aqueous phase which remains following liberation of (R)-1-(4-chlorophenyl)-ethylamine. The solid product which forms is filtered off with suction and dried to give 18.2 kg of (S)-(−)-N-phenylcarbamate lactic acid.

Work-Up of the Mother Liquor

The mother liquor which forms during reaction (a) is combined with the toluene which was used for washing the salt. Toluene is distilled off from the mixture under reduced pressure.

Example 2

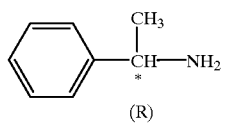

(I-R-2)

(R)

24.2 g (0.2 mol) of racemic 1-phenyl-ethylamine and 17.8 g (0.085 mol) of (S)-(−)-N-phenylcarbamate lactic acid are added to a mixture of 230 g of toluene and 120 g of methanol at room temperature with stirring. The resulting mixture is stirred for 1 hour at 30° C. 230 g of solvent are then distilled off at a maximum sump temperature of 3020 C. with gradual reduction of the pressure. The reaction mixture is then cooled to room temperature and filtered with suction. The solid which forms is washed with a little toluene and dried. This gives 31 kg of product, 81% of which, according to gas-chromatographic analysis, the (R)-1-phenyl-ethylamine salt of (S)-(−)-N-phenylcarbamate lactic acid and 19% of which is the (S)-1-phenyl-ethylamine salt of (S)-(−)-N-phenylcarbamate lactic acid.

The toluene-containing mother liquor which forms after the solid has been removed is free from (S)-(−)-N-phenylcarbamate lactic acid and contains the residual fractions of the 1-phenylethylamine having an S:R isomer ratio of 77.5:22.5.

Example 3

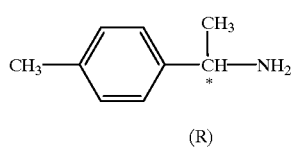

(I-R-3)

(R)

17.8 g (0.085 mol) of (S)-(−)-N-phenylcarbamate lactic acid and 27.0 g (0.2 mol) of racemic 1-(4-methyl-phenyl)-ethylamine are added to a mixture of 230 g of toluene and 120 g of methanol at 30° C. with stirring. After the mixture has been stirred for a further 1 hour at 30° C., 229.7 g of solvent are distilled off at a maximum sump temperature of 30° C. with gradual reduction of the pressure. The reaction mixture is then cooled to room temperature and filtered with suction. The resulting solid is washed with toluene and dried. This gives, in quantitative yield, based on (S)-(−)-N-phenylcarbamate lactic acid used, the (R)-1-(4-methyl-phenyl)-ethylamine salt of (S)-(−)-N-phenylcarbamate lactic acid which, according to gas-chromatographic analysis, has an optical purity of 100%.

The mother liquor produced after the solid has been removed contains the (S)-1-(4-methyl-phenyl)-ethylamine which has not been precipitated as salt, having an S:R isomer ratio of 90.1:9.9.

Example 4

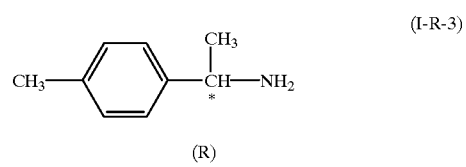

(I-R-3)

(R)

18.8 g (0.09 mol) of (S)-(−)-N-phenylcarbamate lactic acid are added to a mixture of 120 g of methanol and 80 g of toluene at room temperature with stirring. 24.2 g (0.2 mol) of racemic 1-(4-methyl-phenyl)-ethylamine are added to the resulting mixture at 30° C. with stirring. A mixture of methanol and toluene is then distilled off at a constant sump temperature of 30° C. with gradual reduction of the pressure until the bottom product is free from methanol. During distillation, 200 g of toluene are simultaneously added in order that the suspension which forms can still be stirred easily. The reaction mixture is then cooled to 10° C. and filtered with suction. The resulting solid is washed with toluene and dried. This gives, in quantitative yield, based on (S)-(−)-N-phenylcarbamate lactic acid used, a salt, 97.2% of which is the (R)-1-(4-methyl-phenyl)-ethylamine salt of (S)-(−)-N-phenylcarbamate lactic acid and 2.8% of which is the (S)-1-(4-methyl-phenyl)-ethylamine salt of (S)-(−)-N-phenylcarbamate lactic acid.

The mother liquor which forms after the solid has been removed contains the (S)-1-(4-methyl-phenyl)-ethylamine which has not been precipitated as salt, having an S:R isomer ratio of 89.1:10.9.

Example 5

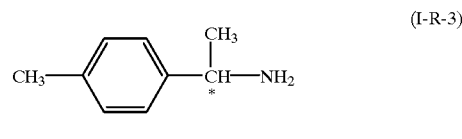

(I-R-3)

(R)

In accordance with the method given in Example 4, 19.9 g (0.095 mol) of (S)-(−)-N-phenylcarbamate lactic acid are reacted with 24.2 g (0.2 mol) of racemic 1-(4-methyl-phenyl)-ethylamin. This gives, in quantitative yield, based on (S)-(−)-N-phenylcarbamate lactic acid used, a salt, 94.2% of which is the (R)-1-(4-methyl-phenyl)-ethylamine salt of (S)-(−)-N-phenyl-carbamate lactic acid and 5.8% of which is the (S)-1-(4-methyl-phenyl)-ethylamine salt of (S)-(−)-N-phenylcarbamate lactic acid.

The mother liquor which forms after the solid has been removed contains the (S)-1-(4-methyl-phenyl)-ethylamine which has not been precipitated as salt, having an S:R isomer ratio of 90.7:9.3.

Example 6

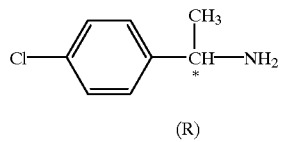
(I-R-1)

(R)

In accordance with the method given in Example 1, 0.2 mol of racemate 1-(4-chloro-phenyl)-ethylamine is in each case reacted with 0.065 mol, 0.07 mol, 0.075 mol.

0.08 mol, 0.085 mol and 0.09 mol of (S)-(−)-N-phenylcarbamate lactic acid. Work-up gives, in each case in quantitative yield, based on (S)-(−)-N-phenylcarbamate lactic acid used, (R)-1-(4-chloro-phenyl)-ethylamine in an optical purity of from 96 to 97%.

The mother liquors which are produced after the solid has been removed contain (S)-1-(4-chloro-phenyl)-ethylamine which has not been precipitated as salt in optical purities between 81 and 90%.

Example 7

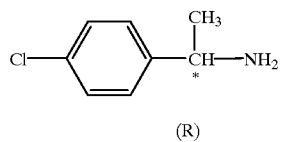
(I-R-1)

(R)

20.7 g (0.133 mol) of racemic 1-(4-chloro-phenyl)-ethylamine and 24.3 g (0.067 mol) of the 1-(4-chloro-phenyl)-ethylamine salt of (S)-(−)-N-phenylcarbamate lactic acid, which contains 0.028 mol of the (R) isomer and 0.039 mol of the (S) isomer of the amine, are added to 413.9 g of methylcyclohexane at room temperature with stirring. The addition of 130 g of methanol and heating to 40° C. cause a clear, two-phase solution to form which contains 0.2 mol of 1-(4-chloro-phenyl)-ethylamine (0.095 mol of the (R) isomer and 0.105 mol of the (S) isomer) and 0.067 mol of (S)-(−)-N-phenylcarbamate lactic acid. A mixture of methanol and methylcyclohexane is then distilled off at a sump temperature of 40° C. with gradual reduction of the pressure until the bottom product is free from methanol. The reaction mixture is then cooled to room temperature and filtered with suction. The resulting solid is washed with toluene and dried. This gives, in quantitative yield, based on (S)-(−)-N-phenylcarbamate lactic acid used, the (R)-1-(4-chloro-phenyl)-ethylamine salt of (S)-(−)-N-phenylcarbamate lactic acid in an optical purity of 98.1%.

Example 8

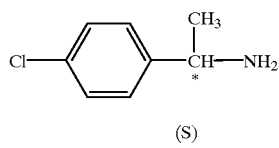
(I-S-1)

(S)

In accordance with the method given in Example 1, 31.1 g (0.2 mol) of racemic 1-(4-chloro-phenyl)-ethylamine are reacted with 18.8 g (0.09 mol) of (S)-(−)-N-phenylcarbamate lactic acid in the presence of 413.9 g of toluene and 117.5 g of methanol. A mixture of methanol and toluene is then distilled off at a maximum sump temperature of 30° C. with gradual reduction of the pressure until the bottom product is free from methanol. During distillation, sufficient toluene is simultaneously added so that the suspension formed can still be stirred easily. The reaction mixture is cooled to 0° C. and the solid produced is filtered off with suction.

4.2 g (0.02 mol) of (S)-(−)-N-phenylcarbamate lactic acid and 19 g of methanol are added to the mother liquor at 40° C. with stirring. A mixture of methanol and toluene is then distilled off at a maximum sump temperature of 40° C. with gradual reduction of the pressure until the bottom product is free from methanol. The solid is filtered off from the resulting suspension with suction and dried. This gives 7.3 g of the salt of racemic 1-(4-chloro-phenyl)-ethylamine and (S)-(−)-N-phenylcarbamate lactic acid. Distillative work-up of the mother liquor gives 15.5 g (0.1 mol) of (S)-1-(4-chloro-phenyl)-ethylamine in an optical purity of 96.1%.

Example 9

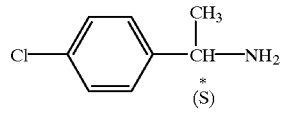
(I-S-1)

(S)

In accordance with the method given in Example 8, 31.1 g (0.2 mol) of racemic 1-(4-chloro-phenyl)-ethylamine are reacted in each case with 0.065 mol, 0.07 mol, 0.075 mol, 0.08 mol and 0.085 mol of (S)-(−)-N-phenylcarbamate lactic acid. An amount of (S)-(−)-N-phenylcarbamate lactic acid which corresponds to twice the difference between 0.1 mol and the initial molar feed of (S)-(−)-N-phenylcarbamate lactic acid is in each case added to the mother liquor which remains after the crystals have been removed. In this connection, the (S)-(−)-N-phenylcarbamate lactic acid is in each case dissolved in methanol prior to the addition, 10 g of methanol being used in each case per 2.0 g (0.01 mol) of (S)-(−)-N-phenylcarbamate lactic acid.

A mixture of methanol and toluene is distilled off from the respective reaction mixture at a maximum sump temperature of 40° C. with gradual reduction in the pressure until the bottom product is free from methanol. The resulting solid is then filtered off with suction and dried. Distillative work-up of the mother liquors produces (S)-1-(4-chloro-phenyl)-ethylamine in a optical purity of 95.0%,
96.0%,
96.2%,
97.9% and
96.4% respectively.

Comparative example A

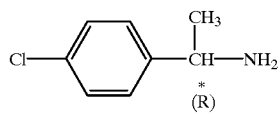
(I-R-1)

In accordance with the method given in Example 1, 31.1 g (0.2 mol) of racemic 1-(4-chloro-phenyl)-ethylamine are in each case reacted with 0.095 mol,
0.1 mol,
0.105 mol and
0.11 mol of (S)-(−)-N-phenylcarbamate lactic acid. Work-up in the manner described above gives, in each case in quantitative yield, based on (S)-(−)-N-phenylcarbamate lactic acid used, the (R)-1-(4-chloro-phenyl)-ethylamine salt of (S)-(−)-N-phenylcarbamate lactic acid. The optical purities of the (R)-1-(4chloro-phenyl)-ethylamine liberated therefrom are between 70 and 80%.

What is claimed is:
1. Process for the preparation of optically active 1-phenyl-ethylamines of the formula

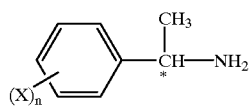
(I*)

in which
  X is hydrogen, halogen or methyl, and
  n is 0, 1 or 2,
  from racemic 1-phenyl-ethyl-amines using (S)-(−)-N-phenylcarbamate lactic acid,
characterized in that
  a) racemic 1-phenyl-ethylamines of the formula

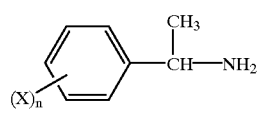
(I)

in which
  X and n are as defined above
  are reacted with (S)-(−)-N-phenylcarbamate lactic acid of the formula

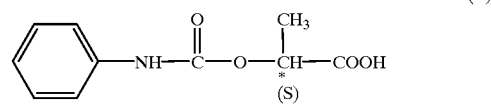
(II)

in the presence of an aliphatic or aromatic hydrocarbon and in the presence of a lower aliphatic alcohol, the amounts of the reaction components being such that per 1 mol of racemic 1-phenyl-ethyl-amine of the formula (I), between 0.25 and 0.5 mol of (S)-(−)-N-phenylcarbamate lactic acid of the formula (II) are present,
  then the lower aliphatic alcohol and, where appropriate, some of the aliphatic or aromatic hydrocarbon are distilled off at a sump temperature up to 40° C., optionally under reduced pressure,
  the resulting crystalline product of the formula

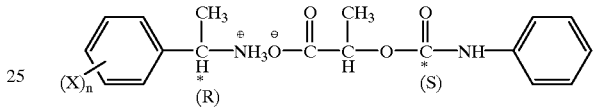
(III-a)

in which
  X and n are as defined above,
  is separated off, stirred with dilute, aqueous alkaline solution in the presence of an aliphatic or aromatic hydrocarbon, the organic phase is separated off, the aqueous phase is again stirred with an aliphatic or aromatic hydrocarbon, the organic phase is again separated off and the combined organic phases are distilled to isolate the (R)-1-phenyl-ethylamine of the formula

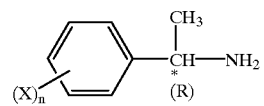
(I-R)

in which
  X and n are as defined above
  which is produced in each case
  and optionally
  b) the mother liquor which remains after the salt of the formula (III-a) has been separated off is reacted, in the presence of a lower aliphatic alcohol, with (S)-(−)-N-phenylcarbamate lactic acid of the formula

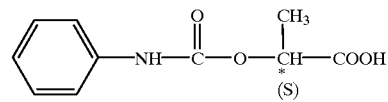
(II)

that the molar amount of (S)-(−)-N-phenylcarbamate lactic acid of the formula (II) is twice the amount of (R)-1-phenyl-ethylamine of the formula (I-R) still present in the mother liquor, then the lower aliphatic alcohol and, where appropriate, some of the aliphatic or aromatic hydrocarbon, are distilled at a sump temperature up to 40° C., optionally under reduced pressure, the resulting crystalline product of the formula

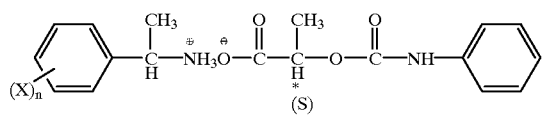
(III-b)

in which
X and n are as defined above
is separated off, and the mother liquor which remains is distilled to isolate the (S)-1-phenyl-ethylamine of the formula

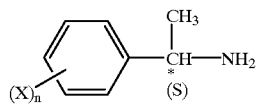
(I-S)

in which
X and n are as defined above,
which is produced in each case.

2. Process according to claim 1, characterized in that the starting materials used are racemic 1-phenyl-ethylamines of the formula (I) in which
X is fluorine, chlorine, bromine or methyl, and
n is 0, 1 or 2.

3. Process according to claim 1, characterized in that the starting material used is racemic 1-(4-chloro-phenyl)-ethylamine.

4. Process according to claim 1, characterized in that the starting material used is racemic 1-(2,4-dichloro-phenyl)-ethylamine.

5. Process according to claim 1, characterized in that the hydrocarbons used are toluene or methylcyclohexane.

6. Process according to claim 1, characterized in that the lower aliphatic alcohol used is methanol.

7. Process according to claim 1, characterized in that the alkaline solution used is aqueous sodium hydroxide solution or aqueous potassium hydroxide solution.

8. Process according to claim 1, characterized in that both the first and also the second stage is carried out at temperatures between −20° C. and +40° C.

9. Process according to claim 1, characterized in that the reaction mixture is evaporated under reduced pressure and at a still temperature of at most 30° C.

10. Process according to claim 1, characterized in that the first stage is carried out using amounts of the reaction components such that per 1 mol of racemic 1-phenyl-ethylamine of the formula (I), between 0.40 and 0.475 mol of (S)-(−)-N-phenylcarbamate lactic acid of the formula (II) is used.

* * * * *